US011202667B2

(12) United States Patent
Horrell et al.

(10) Patent No.: US 11,202,667 B2
(45) Date of Patent: Dec. 21, 2021

(54) METHODS AND DEVICES FOR SEMI-RIGID BONE FIXATION

(71) Applicant: AKROS MEDICAL, INC., Durham, NC (US)

(72) Inventors: Charles Horrell, Durham, NC (US); Nicholas Mourlas, Mountain View, CA (US); Jon Thompson, Fairview, TX (US)

(73) Assignee: AKROS MEDICAL, INC., Durham, NC (US)

( * ) Notice: Subject to any disclaimer, the term of this patent is extended or adjusted under 35 U.S.C. 154(b) by 209 days.

(21) Appl. No.: 16/449,391

(22) Filed: Jun. 22, 2019

(65) Prior Publication Data

US 2019/0374270 A1 Dec. 12, 2019

Related U.S. Application Data

(62) Division of application No. 15/045,224, filed on Feb. 16, 2016, now Pat. No. 10,327,826.

(60) Provisional application No. 62/116,852, filed on Feb. 16, 2015.

(51) Int. Cl.
*A61B 17/86* (2006.01)
*A61B 17/84* (2006.01)
*A61B 17/88* (2006.01)
*A61B 17/90* (2006.01)

(52) U.S. Cl.
CPC .......... *A61B 17/8625* (2013.01); *A61B 17/84* (2013.01); *A61B 17/8875* (2013.01); *A61B 2017/90* (2013.01)

(58) Field of Classification Search
CPC ..... A61B 17/86; A61B 17/864; A61B 17/865; A61B 17/8875
See application file for complete search history.

(56) References Cited

U.S. PATENT DOCUMENTS

| | | | |
|---|---|---|---|
| 5,102,276 A * | 4/1992 | Gourd | F16B 33/006 411/383 |
| 6,458,134 B1 * | 10/2002 | Songer | A61B 17/68 606/304 |
| 6,517,543 B1 * | 2/2003 | Berrevoets | A61B 17/68 411/324 |
| 6,827,285 B2 | 12/2004 | Head | |
| 7,547,324 B2 | 6/2009 | Cragg | |
| 7,905,908 B2 * | 3/2011 | Cragg | A61F 2/4425 606/279 |
| 7,955,388 B2 | 6/2011 | Jensen et al. | |
| 8,048,134 B2 | 11/2011 | Partin | |
| 8,066,748 B2 * | 11/2011 | Lieberman | A61F 2/442 606/279 |
| 9,138,219 B2 * | 9/2015 | Horrell | A61B 17/86 |

(Continued)

*Primary Examiner* — Anu Ramana

(57) ABSTRACT

Apparatus and methods are provided for the approximation of two bones, the apparatus including a first anchor that is rotationally driven into a first bone by a second bone anchor, which receives driving torque from a driver tool. After the first anchor is secured in the first bone, the second anchor is disengaged from the first anchor but remains connected to the first anchor by a flexible link of a designed length. The second bone anchor is secured in the second bone and has provisions to be lengthened or shortened to adjust the overall length of the implant, thereby adjusting the approximation between the two bones.

18 Claims, 17 Drawing Sheets

(56) References Cited

U.S. PATENT DOCUMENTS

| | | | |
|---|---|---|---|
| 2001/0007074 A1* | 7/2001 | Strobel | A61B 17/8877 606/314 |
| 2002/0198527 A1 | 12/2002 | Muckter | |
| 2006/0036240 A1* | 2/2006 | Colleran | A61B 17/7025 606/86 A |
| 2006/0264954 A1 | 11/2006 | Sweeney, II | |
| 2006/0271064 A1 | 11/2006 | Sucec et al. | |
| 2012/0172936 A1 | 7/2012 | Horrell et al. | |

* cited by examiner

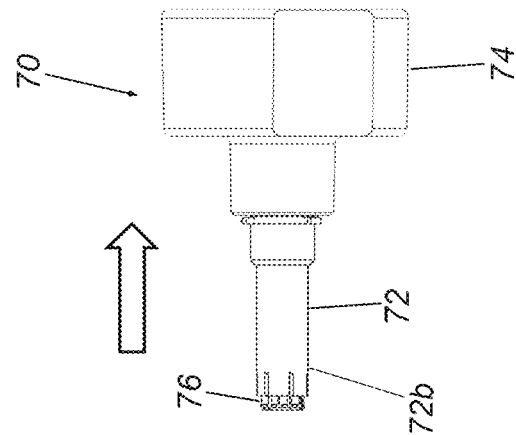
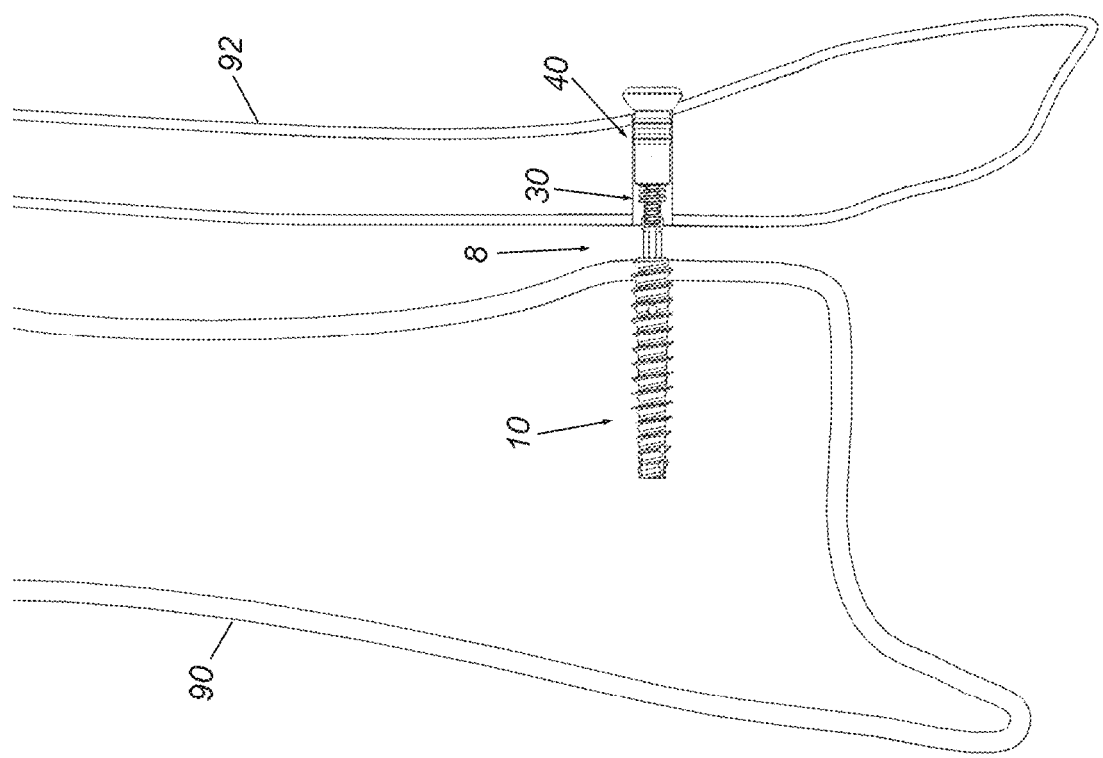
FIG. 13

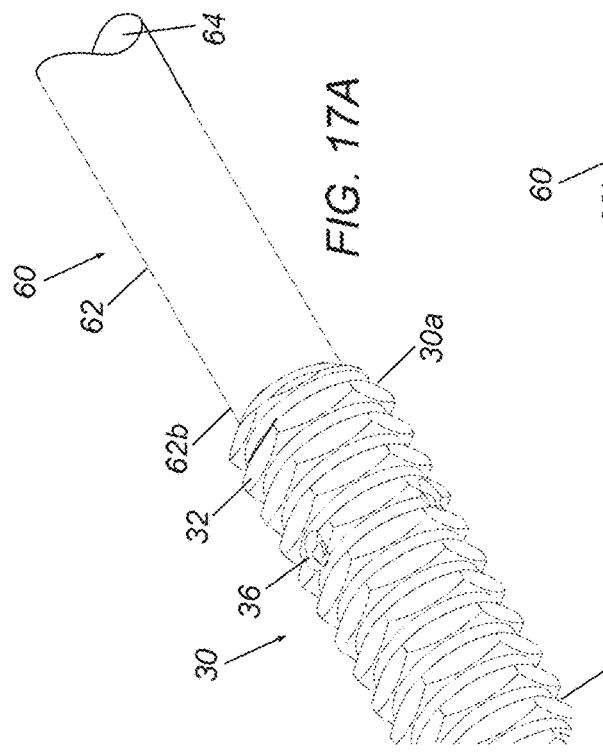
FIG. 17A
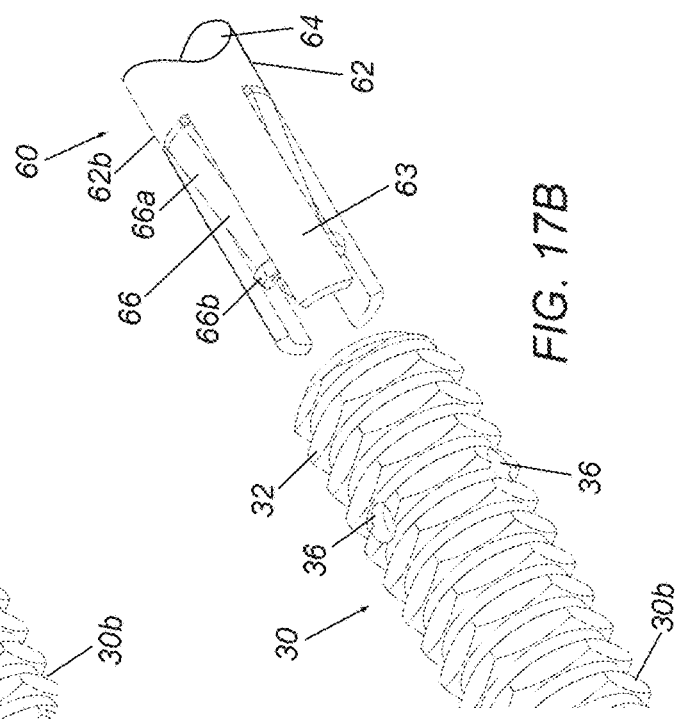
FIG. 17B
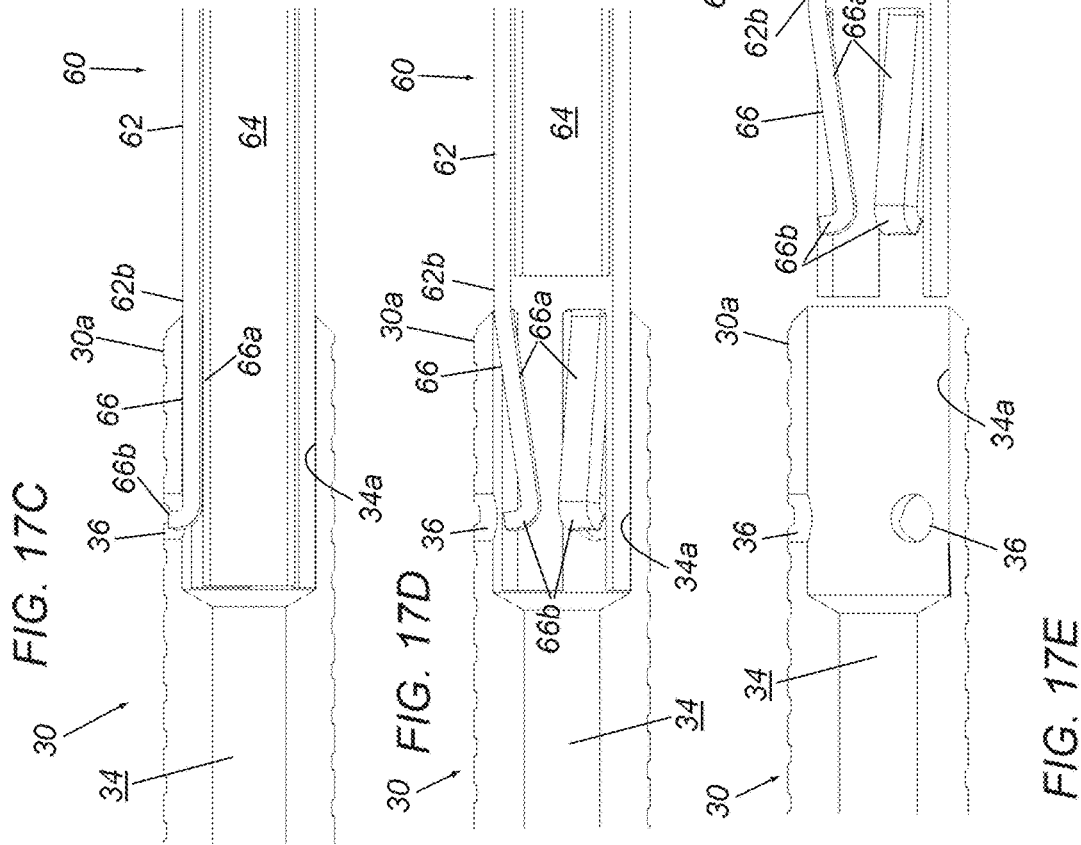
FIG. 17C
FIG. 17D
FIG. 17E

METHODS AND DEVICES FOR SEMI-RIGID BONE FIXATION

RELATED APPLICATION DATA

The present application is a divisional of co-pending application Ser. No. 15/045,224, filed Feb. 16, 2016, issuing as U.S. Pat. No. 10,327,826, which claims benefit of provisional application Ser. No. 62/116,852, filed Feb. 16, 2015, the entire disclosures of which are expressly incorporated by reference herein.

FIELD OF THE INVENTION

The present invention relates to apparatus and methods for semi-rigid fixation of bones. More specifically, certain embodiments relate to systems and methods for fixation of the distal tibia and distal fibula following an injury to the corresponding syndesmotic joint.

BACKGROUND

A syndesmotic injury results when a traumatic injury damages the ligaments that span the gap between the distal tibia and fibula. This can be the result of a high ankle sprain, with no fracture of the fibula, or can also accompany a fibular fracture in a Weber B or Weber C fracture.

A surgeon can determine the presence of a syndesmotic injury by direct visualization of the joint or through radiographic imaging while positioning the ankle in a mortise view orientation. In either case, loads are applied to the joint in either a direct lateral load applied to the fibula or by applying an external rotation load to the foot. While the load is being applied, the relative distance between the fibula and the tibia, the fibula and the talus, and the tibia and the talus are observed to determine the level of damage sustained by the ligaments that typically hold the syndesmotic joint together.

If a syndesmotic injury is found to be present, the typical treatment involves stabilizing the fibula and tibia with respect to each other in the proper orientation and holding them there throughout the soft tissue healing period to allow the ligaments to re-attach and heal. In the event of a syndesmotic injury with a corresponding fibula fracture, this is done while also stabilizing the fibular fracture, which is usually accomplished with a small fracture plate on the lateral side of the fibula. Traditionally the method of stabilization has been to place one or more cortical screws across the syndesmosis, with the head against the lateral face of the fibula and the tip of the screw being in the middle of the tibia or in the medial cortex of the tibia, e.g., as shown in FIG. 1.

This form of treatment provides very rigid fixation, allowing the ligaments to heal, but makes return to weight-bearing more difficult. During a standard gait, the ligaments hold the distance between the tibia and fibula fairly constant, but allow a small amount of shear motion and rotation of the fibula with respect to the tibia. The presence of the fixation screws prevents this motion and can cause discomfort and limited flexibility of the ankle joint. Typically, the surgeon prescribes a secondary surgery to remove the screws once the ligaments have healed. In some cases, a surgeon may simply recommend a return to weight-bearing when the ligaments have healed and, after a period of time of loading the screws, they will experience a fatigue failure and normal anatomical motion will be restored.

Accordingly, apparatus and methods for providing semi-rigid fixation of the distal tibia and fibula following a syndesmotic injury would be useful.

SUMMARY

The present invention is directed to apparatus and methods for stabilizing a joint between two bones, e.g., during the soft tissue healing period following a traumatic injury.

In an exemplary application, the apparatus and methods herein may be configured to provide substantially rigid tensile fixation between the tibia and fibula while allowing the small amount of shear and rotational motion required for a standard gait. This may make it possible for patients to return to weight-bearing earlier, which may improve clinical outcomes, and/or may also reduce the number of follow-up hardware-removal surgeries.

In accordance with one embodiment, an apparatus is provided for placing a first anchor in a first bone such as a tibia, a second anchor in a second bone such as a fibula, the two anchors being connected by a flexible member that provides substantial tensile stabilization but offers little or no resistance to bending, rotation, or shear motion of the two anchors with respect to each other. In this embodiment, the first anchor may have an external threadform allowing it to be advanced completely into the tibia leaving no rigid hardware in the joint space. Further, the second anchor may include a distal piece and a proximal piece, the distal piece of which has an external threadform mated to an internal threadform in the proximal piece, allowing precise adjustment of the overall length of the construct and therefore the amount of tensile compression applied to the joint.

In accordance with another embodiment, a method is provided for delivering this system in which a driver is used to impart the torque required to install the first anchor into the first bone. This torque is not applied directly to the first anchor, but is applied through the distal piece of the second anchor, which is coupled to the first anchor during the early deployment steps. Once the first anchor is properly placed, this coupling is released by the surgeon, and the distal piece of the second anchor is allowed to disengage and retract to its position in the second bone. Rotation of this distal piece of the second anchor is controlled by another installation tool while the proximal piece is coupled to it and adjusted to the desired position. This desired position is infinitely adjustable and should result in the proper amount of joint correction. Once the desired position is reached, all installation tools are released and withdrawn by the surgeon, leaving only the implant construct.

In accordance with still another embodiment, an apparatus is provided for that has a first anchor with features other than an external threadform to attach it to the first bone. In exemplary embodiments, these features may include barbs or wings that are deployed by the surgeon. In the same way, the coupling between the distal and proximal pieces of the second anchor may be accomplished using features other than a threadform. In exemplary embodiments, these features may include a ratchet and pawl mechanism or a friction fit that may be tightened by the surgeon when the proper placement is reached.

In accordance with yet another embodiment, an apparatus is provided for the approximation of two bones that includes a first anchor comprising a proximal end, a distal end configured for insertion into a first bone, and a bore extending from the proximal end towards the distal end, the bore including a proximal region defining a plurality of walls, and an intermediate region distal to the proximal region including a first mount, and a second anchor. The second anchor includes a first component including a proximal end, a distal end sized to be inserted into the proximal region of the bore in a delivery configuration and having a predetermined shape such that the distal end engages the plurality of walls in the delivery configuration to transfer torque or other forces from a driver tool coupled to the first component to the first anchor, and a second mount; a second component including a tubular body sized to be advanced over the first component proximal end and including one or more features for cooperating with one or more corresponding features on the first component to control advancement of the second component over the first component, and an enlarged head on a proximal end of the tubular body; and a flexible link extending between the first and second mounts for limiting spacing of the first component from the first anchor when the first component distal end is disengaged from the proximal region of the bore in a deployed configuration.

In accordance with another embodiment, a system is provided for the approximation of first and second bones that includes a first driver tool comprising a proximal end, a distal end, a lumen extending between the driver tool proximal and distal ends, and a socket in the distal end; a guide member slidably inserted into the first driver tool lumen and including a distal end including one or more connectors disposed adjacent the first driver tool distal end; and an implant. The implant includes a first anchor comprising a proximal end, a distal end configured for insertion into a first bone, and a bore extending from the proximal end towards the distal end, and an intermediate region distal to the proximal region including a first mount; a first component for a second anchor comprising a proximal end received in the socket of the first driver tool, a distal end extending from the first driver tool distal end and received in the proximal region of the bore and shaped to engage the first anchor to transfer torque or other forces from the first driver tool to the first anchor to insert the first anchor into a first bone, a second mount adjacent the distal end, and one or more mating connectors engaged with the one or more connectors of the guide member; a second component for the second anchor including a tubular body sized to be advanced over the first component proximal end when the first driver tool is removed after inserting the first anchor into bone to expose the proximal end of the first component, and an enlarged head on a proximal end of the tubular body, the tubular body including one or more features for cooperating with one or more corresponding features on the first component to control advancement of the second component over the first component; and a flexible link extending between the first and second mounts for limiting spacing of the first component from the first anchor when the first component distal end is disengaged from the proximal region of the bore. Optionally, the system may also include a second installation tool engageable with the head of the second component for directing the second component over the first component to adjust an overall length of the implant, thereby adjusting the approximation between the first and second bones.

In accordance with still another embodiment, a method is provided for approximating first and second bones relative to one another that includes advancing a first anchor into a first bone by applying a torque or other force to a driver tool coupled to a first component of a second anchor, the first component coupled to the first anchor; disengaging the first component of the second anchor from the first anchor to expose a flexible link extending between the first anchor and the first component of the second anchor; withdrawing the second anchor until the flexible link connecting the two reaches its designed length, thereby positioning the second anchor in a second bone; affixing a second component of the second anchor to the first component of the second anchor such that a head of the second component engages the second bone or a bone support on the second bone; and adjusting a location of the second component along the first component to adjust the approximation between the first and second bones.

In accordance with yet another embodiment, a method is provided for approximating first and second bones relative to one another that includes providing a driver tool including a shaft having a distal end, a first anchor, a first component of a second anchor including a distal end received in a first socket of the first anchor, and a proximal end received in a second socket in the driver tool shaft distal end, and a guide member coupled to the first component proximal end and extending proximally through the driver tool shaft, the first anchor and first component secured relative to the driver tool shaft distal end; advancing the first anchor towards a first bone through a hole in a second bone adjacent the first bone; applying a torque or other force to the driver tool to direct the first anchor into the first bone, the force transferred from the driver tool shaft to the first anchor via the first component of the second anchor; releasing the first anchor and first component from the driver tool shaft distal end; withdrawing the driver tool, thereby exposing the guide member; directing a second component of the second anchor over the guide member to the first component; advancing the second component of the second anchor over the first component, thereby causing the first component distal end to withdraw from the first socket and expose a flexible link extending between the first anchor and the first component of the second anchor; advancing the second component further, thereby extending the flexible link to a predetermined or designed length and positioning the second anchor in the hole in the second bone; engaging a head of the second component with the second bone or a bone support on the second bone; and adjusting a location of the second component along the first component to adjust the approximation between the first and second bones.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 5-14 are cross-sectional views of a tibia and fibula showing an exemplary method for installing an implant, such as that shown in FIG. 2.

FIG. 5 is a depiction of a K-wire and step-drill being used to prepare the implant site.

FIG. 6 shows a first anchor being placed in the tibia using a first anchor driver tool.

FIG. 7A shows a suture on a handle of the first anchor driver tool that keeps the first anchor driver tool, the distal piece of the second anchor, and the first anchor engaged.

FIG. 7B shows the suture being released to release the first and second anchors from the first anchor driver tool.

FIG. 8 shows the first anchor driver tool being retracted, exposing a distal component of the second anchor and guide tube that is coupled to the second anchor to control its motion.

FIG. 9 is a detail showing the engagement of the distal component of the second anchor with the guide tube and the first anchor.

FIG. 10A shows the proximal component of the second anchor being directed over the guide tube using a second anchor installation tool, and engaging a back end of the first anchor driver tool with the guide tube.

FIG. 10B is a detail showing the first anchor driver tool being engaged with the guide tube to control the motion of the guide tube.

FIG. 11 shows the proximal component of the second anchor being threaded over the distal component, thereby causing the distal component to disengage from the first anchor and exposing a flexible link between the two anchors.

FIG. 12 shows the guide tube being removed after the proximal component is tightened to a desired position and implant placement is finalized.

FIG. 13 shows the second anchor installation tool being disengaged from the proximal component of the second anchor and withdrawn.

FIG. 14 shows the implant in its completely-installed state.

FIGS. 17A-17E are various details of exemplary connectors on the distal component of the second anchor and the guide tube for releasably securing the distal component to the guide tube.

DETAILED DESCRIPTION OF THE
EXEMPLARY EMBODIMENTS

Figure 1:
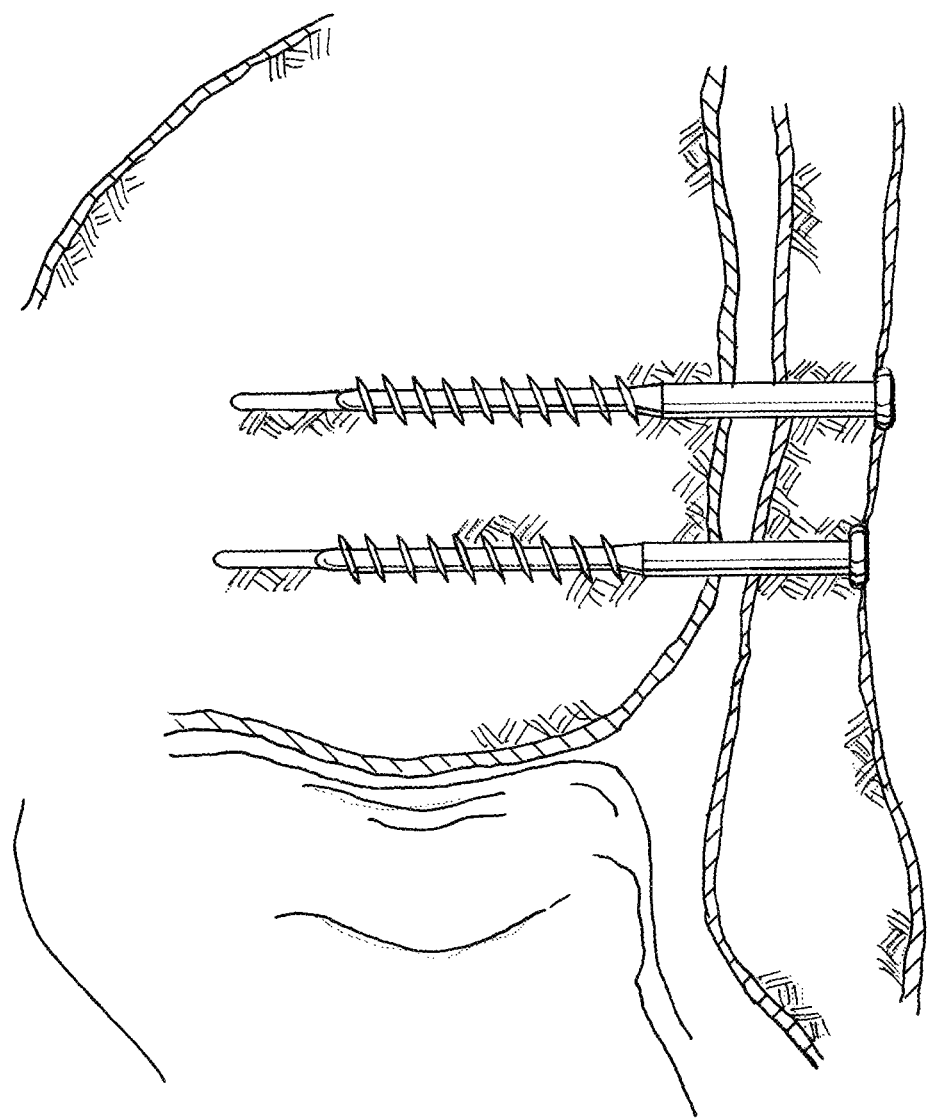
FIG. 1 is a mortise view of an ankle joint showing fixation with cortical screws.
Figure 2:
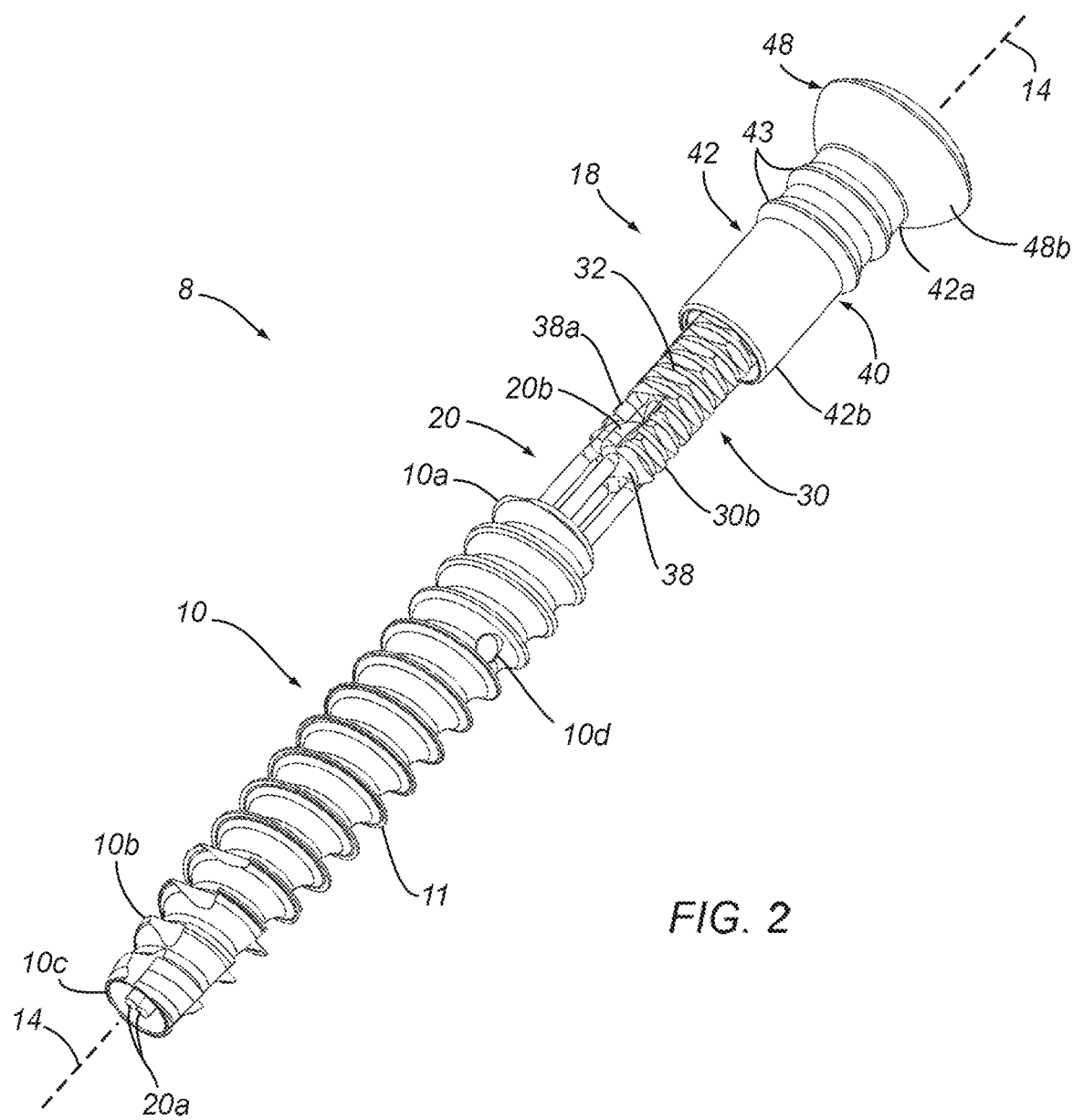
FIG. 2 is a perspective view of an exemplary embodiment of an implant for providing semi-rigid fixation between two bones.
Figure 3:
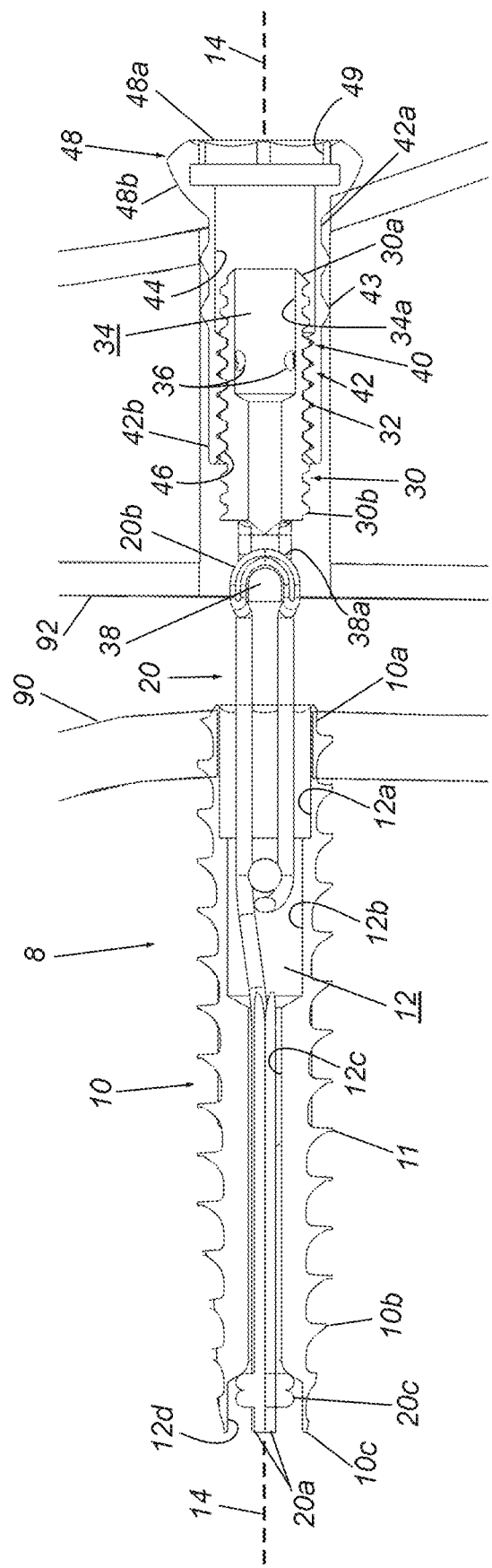
FIG. 3 is a cross-sectional view of the implant of FIG. 2 as installed in a tibia and fibula.
Figure 4:
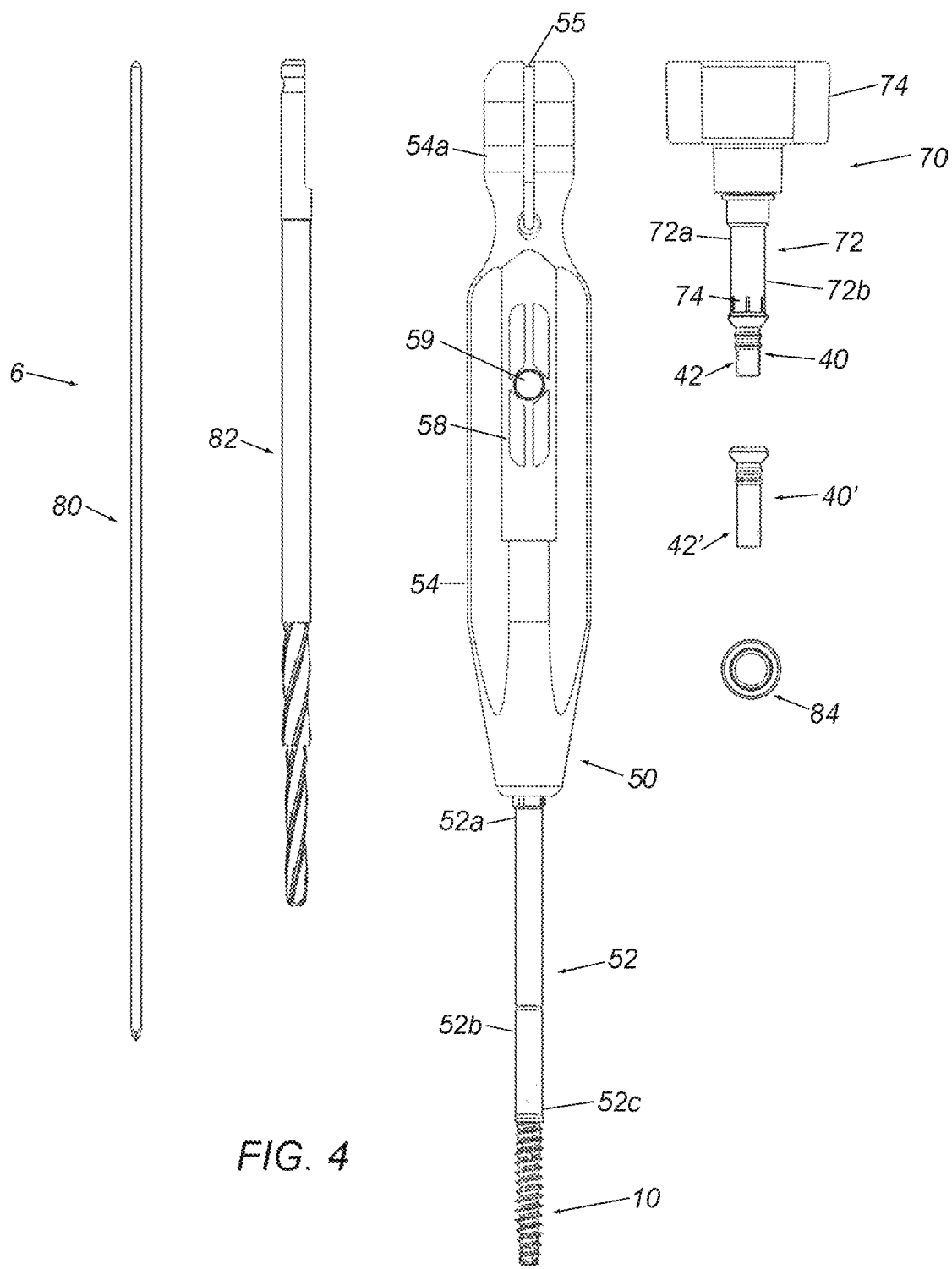
FIG. 4 shows an exemplary embodiment of an entire kit, including an implant, such as that shown in FIG. 2, and its delivery tools.

Turning to the drawings, FIGS. 2 and 3 show an exemplary embodiment of a device or implant 8 for providing semi-rigid fixation between two bones that generally includes a first anchor 10 configured for insertion into a first bone, e.g., a tibia 90 (shown in FIG. 3), a second anchor 18 for engaging a second bone adjacent the first bone, e.g., a fibula 92 (shown in FIG. 3), and a flexible link 20 extending between the first and second anchors 10, 18, e.g., to provide approximation between the first and second bones 90, 92. The second anchor 18 generally includes a first or distal component 30 coupled to the first anchor 10 by the flexible link 20 and a second or proximal component 40 configured to be threaded over the first component 30 for engaging the second bone 92. Optionally, one or more tools and/or accessories may also be provided, e.g., to provide a system or kit for installing the implant 8. For example, as shown in FIG. 4, a system 6 may be provided that includes a first driver tool 50 for inserting the first anchor 10 into bone and a second installation tool 70 for advancing the second component 40 of the second anchor 18 over the first component 30. Optionally, the system 6 may also include a length of Kirschner wire 80, a custom step drill 82, and/or a washer 84, as described elsewhere herein.

Returning to FIGS. 2 and 3, the first anchor 10 is a rigid elongate member including a proximal end 10a, a distal end 10b configured for insertion into a first bone and terminating at a distal tip 10c, one or more external threads 11 extending at least partially between the proximal and distal ends 10a, 10b, and a bore 12 extending from the proximal end 10a at least partially towards the distal end 10b, generally along a longitudinal axis 14 of the implant 8. In an exemplary embodiment, best seen in FIG. 3, the bore 12 includes a proximal region 12a, an intermediate region 12b distal to the proximal region 12a including a first support structure 16 therein, and a distal region 12c extending from the intermediate region 12b to a recess 12d in the distal tip 10c. The proximal region 12a may include a plurality of walls, e.g., defining a polygonal shape, such as a triangular, square, pentagonal, hexagonal, octagonal shape, and the like, to provide a socket for receiving the first component 30 of the second anchor 18, as described elsewhere herein. The intermediate region 12b and distal region 12c may have a circular or other desired cross-sectional shape, with the distal region 12c having a diameter or other maximum cross-section smaller than the intermediate region 12b. The recess 12d may have a diameter or other cross-section larger than the distal region 12c, e.g., to receive a knot 20c or otherwise fixed ends 20a of the flexible link 20, as described elsewhere herein.

The first support structure 16 may be provided within the bore 12, e.g., across the intermediate region 12b substantially perpendicular to the longitudinal axis 14. In an exemplary embodiment, holes 10d may be provided through opposite side walls of the first anchor 10 into the intermediate region 12b and a pin 16 may be inserted into the holes 10d such that the pin 16 extends across the intermediate region 12b and substantially permanently attached thereto, e.g., by one or more of press-fit or other interference fit, bonding with adhesive, sonic welding, soldering, and the like. In an alternative embodiment, the holes 10d may be omitted and a pin may be inserted through the proximal region 12a of the bore and positioned and fixed across the intermediate region 12b, e.g., by one or more of interference fit, bonding with adhesive, sonic welding, soldering, and the like. In another alternative, a support structure may be integrally formed with the first anchor 10, e.g., machined, cast, molded, and the like from the same piece of material as the rest of the first anchor 10. The pin or other support structure 16 generally has a diameter or other cross-section smaller than the intermediate region 12b such that the flexible link 20 may be wrapped at least partially around the support structure 16, as described further elsewhere herein.

The external threads 11 may extend from the proximal end 10a helically towards the distal end 10b, e.g., entirely to the distal tip 10c or the threads 11 may terminate before the distal tip 10c, e.g., to provide a smooth-walled, unthreaded distal tip (not shown). The threads 11 may have a substantially uniform configuration along the threaded region of the first anchor 10 or the threads 11 may be varied as desired, e.g., having different heights, edges, and/or axial spacing (threads per millimeter), as desired.

Optionally, as can be seen in FIG. 3, the threads 11 may end before the proximal-most edge of the first anchor 10, e.g., about half to one millimeter (0.5-1.0 mm). Such an offset may facilitate identifying the end of the first anchor 10, e.g., to identify the interface between the first anchor 10 and the first driver tool 50 (not shown, see FIG. 4). In addition, the offset may provide an unthreaded region on the proximal end 10a in case the first anchor 10 extends a small distance from a bone into which it is implanted, which may reduce risk of irritation and/or damage to adjacent tissue.

With continued reference to FIGS. 2 and 3, the first component 30 of the second anchor 18 is an elongate rod or tubular body including a proximal end 30a, a distal end 30b, and one or more external threads 32 extending at least partially between the proximal and distal ends 30a, 30b. In addition, the first component 30 may have an outer profile to facilitate coupling the first component 30 between the first driver tool 50 (not shown) and the first anchor 10. For example, as best seen in FIG. 2, the first component 30 may have a substantially uniform hexagonal outer profile along its length with the threads 32 conforming to the outer profile. The outer profile generally corresponds to the size and shape of the proximal region 12a of the bore 12 in the first anchor 10, thereby allowing the distal end 30b of the first component 30 to be inserted into the proximal region 12a. Similarly, the proximal end 30a may have an outer profile corresponding to a lumen, recess, or other passage in the first driver tool 50 such that the proximal end 30a may be inserted into the first driver tool 50, e.g., as shown in FIG. 4, thereby causing the first component 30 to transfer torque from the first driver tool 50 to the first anchor 10, as described further elsewhere herein. It will be appreciated that the proximal and distal ends 30a, 30b may have similar profiles (e.g., the first component 30 may have a substantially uniform shape along its length), or the proximal and distal ends 30a, 30b may have different shapes and/or sizes as long as they correspond to the size and shape of the sockets in the first anchor 10 and first driver tool 50 that receive them.

In addition, as shown in FIG. 3, the first component 30 may include a bore or passage 34 therein, e.g., extending partially or entirely from the proximal end 30a to the distal end 30b. The bore 34 may include a proximal region 34a sized to receive a guide tube or member 60 (not shown, see, e.g., FIGS. 8 and 9) and including one or more pockets or other connectors 36 configured to engage corresponding connectors 66 on the guide tube 60 (not shown, see, e.g., FIGS. 17A-17E), as described elsewhere herein.

The first component 30 also includes a second mount or support structure 38, e.g., adjacent the distal end 30b for coupling the flexible link 20 to the first component 30. In the exemplary embodiment shown, an aperture or passage 38a is provided that extends through the first component 30 adjacent the distal end 30b, e.g., through opposite side walls thereof substantially perpendicular to the longitudinal axis 14. The passage 38a may have rounded surfaces and the like to accommodate wrapping a portion of the flexible link 20 through the passage 38a and at least partially around the second mount 38.

In an exemplary embodiment, the flexible link 20 may be an elongate length of suture or other filament having first and second ends 20a. During assembly, one of the ends 20a may be directed through the passage 38a until a central region 20b is disposed around the second mount 38, thereby defining a loop. The ends 20a may then be directed into the bore 12 of the first anchor 10, e.g., into the proximal region 12a, into the intermediate region 12b, wrapped at least partially around the first mount 16, and then into the distal region 12c until the ends 20a exit the bore 12 at the distal tip 12d. The ends 12a may then be secured together, e.g., by tying one or more knots seated within the recess 12d that have a cross-section larger than the distal region 12a, thereby preventing the ends 20a from being pulled back through the bore 12 during implantation. Alternatively, one of the ends 20a may be directed through the bore 12 from the distal tip 10c, wrapping the end at least partially around the first mount 16, exiting the proximal region 12a, wrapping the end 20a around the second mount 38 and back through the bore 12 before tying the knot within the recess 12d.

The knot of the ends 20a may be tied to provide a predetermined length of suture from the ends 20a to the loop 20b around the second mount 38, thereby providing a desired maximum spacing between the first anchor 10 and the first component 30 of the second anchor 18, as described elsewhere herein. For example, the length of the suture 20 may be set such that the maximum spacing between the proximal end 10a of the first anchor 10 and the distal end 30b of the first component 30 may be between about two and four millimeters (2-4 mm).

In alternative embodiments, other configurations may be provided for the flexible link 20 to flexibly connect the first anchor 10 and the first component 30. For example, a central region of a suture may be wrapped around the first mount 16 and the ends 20a may be secured together within the first component 30, e.g. within a recess (not shown) in the distal end 30b beyond the second mount 38. In addition or alternatively, the ends 20a may be secured together by one or more of crimping a sleeve (not shown) over the ends 20a, fusing, bonding with adhesive, and the like in addition to or instead of knotting.

With continued reference to FIGS. 2 and 3, the second component 40 of the second anchor 18 generally includes an elongate tubular body 42 including a proximal end 42a, a distal end 42b, and a passage 44 extending at least partially from the distal end 42b towards the proximal end 42a. The passage 44 is sized to be advanced over the proximal end 30a of the first component 30 and includes one or more internal threads 46 for cooperating with the external threads 32 on the first component 30, e.g., to allow the second component 40 to be controllably advanced over the first component 30.

In addition, the second component 40 includes an enlarged head 48 on the proximal end 42a, e.g., including a substantially flat or otherwise shaped proximal surface 48a and a flared or other expanding distal surface 48b, e.g. for engaging the second bone 92 as shown in FIG. 3. As shown in FIG. 3, the head 48 may include a connector or other interface 49 for engaging the second component 40 with the second installation tool 70 (not shown, see, e.g., FIG. 4). For example, the connector 49 may be a shaped recess including one or more pockets or detents, and the second installation tool 70 may include corresponding connector(s) 76 that may engage the connector 49 to secure the second component 40 to the second installation tool 70, yet allow the second installation tool 70 to be disengaged when a predetermined force or other action is performed, as described elsewhere herein.

Optionally, the tubular body 42 may include one or more annular ridges or other features 43 on an outer surface of the tubular body 42, e.g., adjacent the proximal end 42a. For example, the tubular body 42 may have an outer diameter smaller than a clearance hole drilled in bone through which the second component 40 is introduced, and the annular ridges 43 may have a diameter similar to the clearance hole such that ridges 43 may contact surrounding bone to secure the tubular body 42 within the bone, e.g., once bony ingrowth occurs.

Turning to FIG. 4, an exemplary embodiment of an entire kit is shown that may be included in a system 6 for performing a procedure including implantation of an implant 8, such as that shown in FIG. 2. As shown, the kit generally includes a Kirschner wire 80 and a custom step drill 82 for site preparation, the first anchor 10, e.g., optionally preloaded into the first driver tool 50, which houses many of the other components during the early phases of installation, and the second component 40 of the second anchor 18, e.g., optionally loaded onto the second installation tool 70.

Optionally, a plurality of second components may be provided, e.g., the set of second components 40, 40' shown in FIG. 4, that have different dimensions such that an appropriate second component may be selected based on the individual patient anatomy encountered. For example, as shown, a standard second component 40 may be provided having a standard size (i.e., length) and a large size second component 40' may be provided having a longer tubular body 42' for situations when the installed implant construct needs to have a longer overall length. In another option, the system 6 may include a washer 84 included in the kit, which may be used in cases where the load of the second anchor 18 needs to be spread out over a larger contact area of bone, such as in osteoporotic patients with poor bone quality.

As shown in FIG. 4, the first driver tool 50 generally includes an elongate tubular outer shaft 52 including a proximal end 52a having a handle 54 thereon, a distal end 52b terminating in a distal tip 52c, and a lumen (not shown) extending between the proximal and distal ends 52a, 52b. The distal tip 52c includes a recess or other socket (not shown) sized and/or shaped to receive the proximal end 30b of the first component 30 of the second anchor 18, as described elsewhere herein. Optionally, the handle 54 includes one or more additional features, e.g., a cleating structure 58 and an actuator 59 for releasably securing a suture or other filament 56 used to secure the first anchor 10 and/or first component 30 to the first driver tool 50, as described elsewhere herein.

In addition, as shown in FIGS. 8-10B, the first driver tool 50 includes a guide tube or member 60 including an elongate inner shaft 62 sized to slidably fit within the lumen of the outer shaft 52, e.g., defining an outer diameter smaller than the inner diameter of the lumen of the outer shaft 52. The inner shaft 62 includes a proximal end 62a, a distal end 62b including one or more detents or other connectors 66 for securing the first component 30 of the second anchor 18 to the guide tube 60, and a lumen 64 extending therebetween, e.g., for receiving a lock tube or member 86.

For example, FIGS. 17A-17C show an exemplary embodiment of cooperating connectors 36, 66 that may be provided on the first component 30 and the guide tube 60. In the embodiment shown, the first component 30 includes three pockets or holes 36 and the guide tube 60 includes three corresponding fingers or connectors 66, although it will be appreciated that fewer (e.g., one or two) or more connectors 36, 66 may be provided, as desired. Each connector 66 includes a cantilevered arm 66a and a detent 66b carried on a free end of the arm 66a. The arms 66b may be biased to an inward orientation, e.g., as shown in FIGS. 17B, 17D, and 17E, yet may be directed outwardly, e.g., as shown in FIG. 17C, to engage the pockets 36. The guide tube 60 may also include stationary arms 63, e.g., extending axially between each connector 66 such that the arms 63 may slide into the proximal region 34a of the bore 34 in the first component 30.

During assembly, the distal end 62b of the inner shaft 62 may be inserted into the proximal end 30a of the first component 30, i.e., with the connectors 66 in their inward orientation, as shown in FIGS. 17D and 17E, and the detents 66b may be aligned with respective pockets 36 in the first component 30. Once properly positioned, the lock member 86 may be inserted into the lumen 64 from the proximal end 62a of the inner shaft 62 until a distal end of the lock member 86 (not shown) is inserted into the distal end 62b and the connectors 66. The size of the lock member 86 may be such that its distal end slidably engages the arms 66a of the connectors 66, thereby directed them outwardly and inserting the detents 66b into the pockets 36, as best seen in FIG. 17C. Thus, in this manner, the first component 30 cannot move axially and/or rotate about the longitudinal axis 14 since it is coupled to the guide tube 60.

The outer shaft 52 of the first driver tool 50 may then be advanced over the guide tube 60 until the distal 52b is adjacent the first component 30, whereupon the proximal end 30a of the first component 30 may be received within the distal end 52b of the outer shaft 52. The first anchor 10 may then be inserted over the distal end 30b of the first component 30 and the assembly secured, e.g., using the suture 56, as described elsewhere herein. The first driver tool 50 may subsequently be provided to an end user in this configuration, i.e., with the first anchor 10 and first component 30 secured to the distal end 52b of the outer shaft 52 and the guide tube 60 and locking member 86 inside the outer shaft 52.

Optionally, returning to FIGS. 10A and 10B, the proximal end 62a of the inner shaft 62 may include one or more gripping features 63. For example, the gripping features 63 may include a plurality of holes, tabs, and the like that may be engaged by a tool to prevent movement of the guide tube while performing other operations, e.g., advancing the second component 40 of the second anchor 18 over the guide tube 60, as described elsewhere herein. For example, as shown, the handle 54 of the first driver tool 50 may include a back end 54a that includes a receptacle or other passage 55 sized to receive the proximal end 62a of the guide tube 60. The back end 54a may include a slot 54b extending axially along the back end 54a and radially inwardly to the receptacle 55 such that the back end 54a is compressible to reduce the size of the receptacle 55. Thus, during use, the proximal end 62a of the guide tube 60 may be inserted into receptacle 55, whereupon the back end 54a may be squeezed or otherwise compressed to engage the guide tube 60 until the back end 54a is released, as described elsewhere herein.

In addition, the first driver tool 50 includes one or more features for releasably securing the first anchor 10 relative to the shaft 52. For example, as shown in FIGS. 7A and 7B, a suture or other filament 56 may be provided that extends from the handle 54 through the lumen of the outer shaft 52 to the first anchor 10 and/or first component 30 where the suture 56 is looped around a portion of the flexible link 20, e.g., between the first anchor 10 and the first component 30, first anchor 10 and/or first component 30 where the suture 56 is looped around a portion of the flexible link 20, e.g., between the first anchor 10 and the first component 30, and returns back to the handle 54. This routing may provide a mechanical advantage and hold the first anchor 10 tightly against the first component 30 and outer shaft 52. Alternatively, the suture 56 may be looped around other components, e.g., the pin 16 within the first anchor, and returned to the handle. The suture 56 may be tightened during assembly such that the first component 30 of the second anchor 18 and the first anchor 10 are secured to the shaft 52 with the first component 30 received in the sockets of both the first anchor 10 and the shaft 52, thereby holding the components to the first driver tool 50 during introduction, as described elsewhere herein. The ends 56a of the suture 56 may be secured to the handle 54 such that at least one of the ends 56a may be released when desired. For example, a first end 56a of the suture loop 56 may be secured through a cleating structure 58 on the handle 54 and the handle 54 may include an actuator 59 that may activated to release the first end 56a such that the now-free first end 56a retreats into the driver shaft 52 as the driver is withdrawn from the first anchor 10 to release the first anchor 10 (and the first component 30) and allow subsequent separation.

Turning to FIGS. 5-14, an exemplary method is shown for installing the implant 10 shown in FIGS. 2 and 3 between a tibia 90 and a fibula 92, e.g., using the system 6 shown in FIG. 4, to provide semi-rigid fixation of the bones relative to one another, e.g., to treat a syndesmotic injury. It will be appreciated that the implants, systems, and methods described herein may also be used in other locations and/or procedures, e.g., to provide approximation between two bones other than the tibia and fibula.

Figure 5:
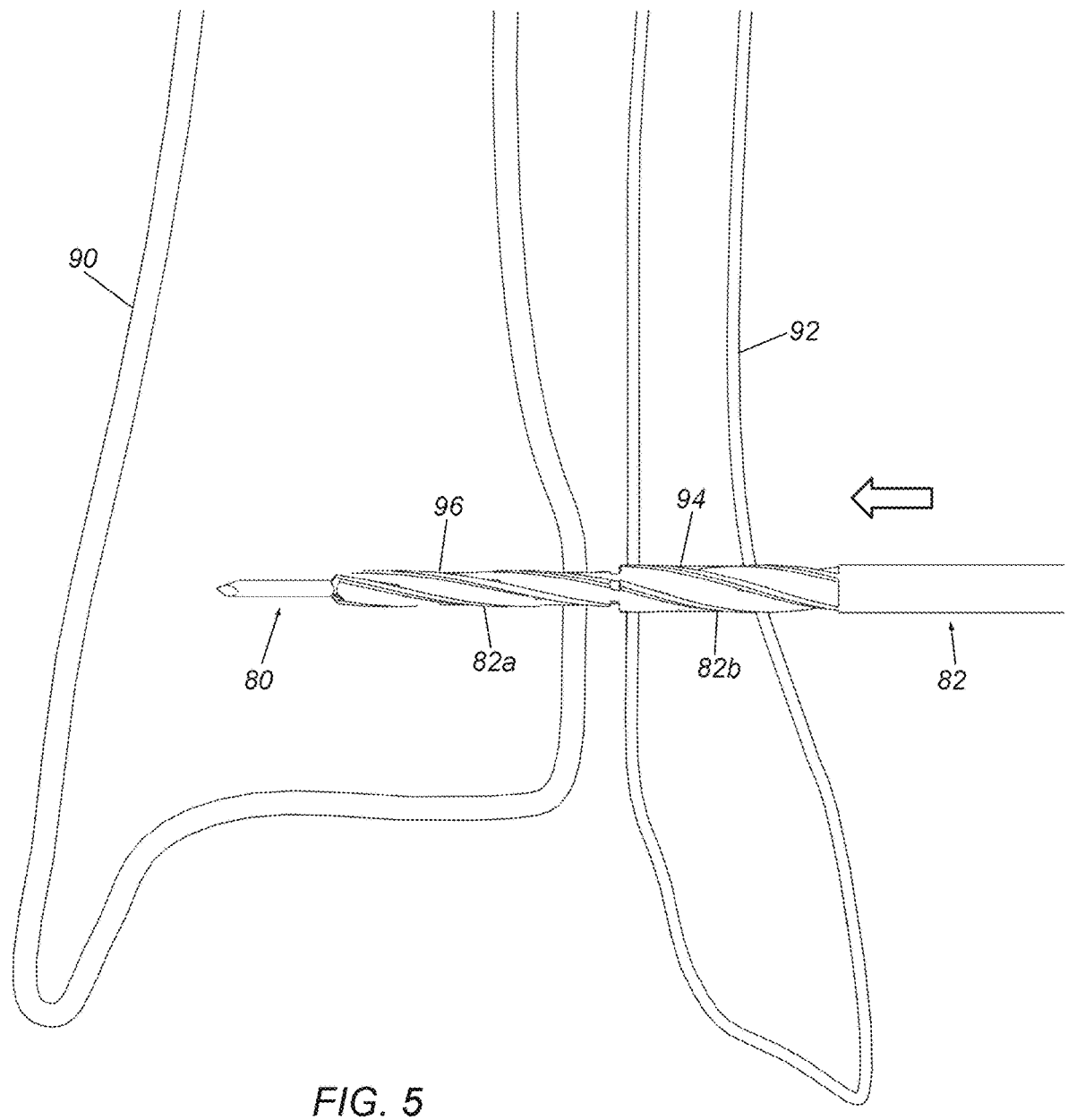

Initially, as shown in FIG. 5, the Kirschner wire may be placed through the fibula 92 and into the tibia 90 at the appropriate location, e.g., using conventional methods, and then a drill may be introduced over the Kirschner wire to create a hole 94 through the fibula 92 and at least partially into the tibia 90. In the exemplary embodiment shown in FIG. 4, the drill may use a custom step drill bit 82 that includes a relatively smaller-diameter distal portion 82a that creates a smaller pilot hole 96 in the tibia 90 and a relatively larger-diameter proximal portion 82b creates a larger clearance hole 94 through the fibula 92. In an exemplary embodiment, the distal portion 82a may be sized to create a pilot hole no larger than about three millimeters (3 mm) in diameter, and the proximal portion 82b may be sized to create a clearance hole larger than four millimeters (4.0 mm), e.g., about 4.1 mm, to accommodate a first anchor having an outer thread diameter of four millimeters (4.0 mm). It will be appreciated that other sizes may be provided, as desired.

Figure 6:
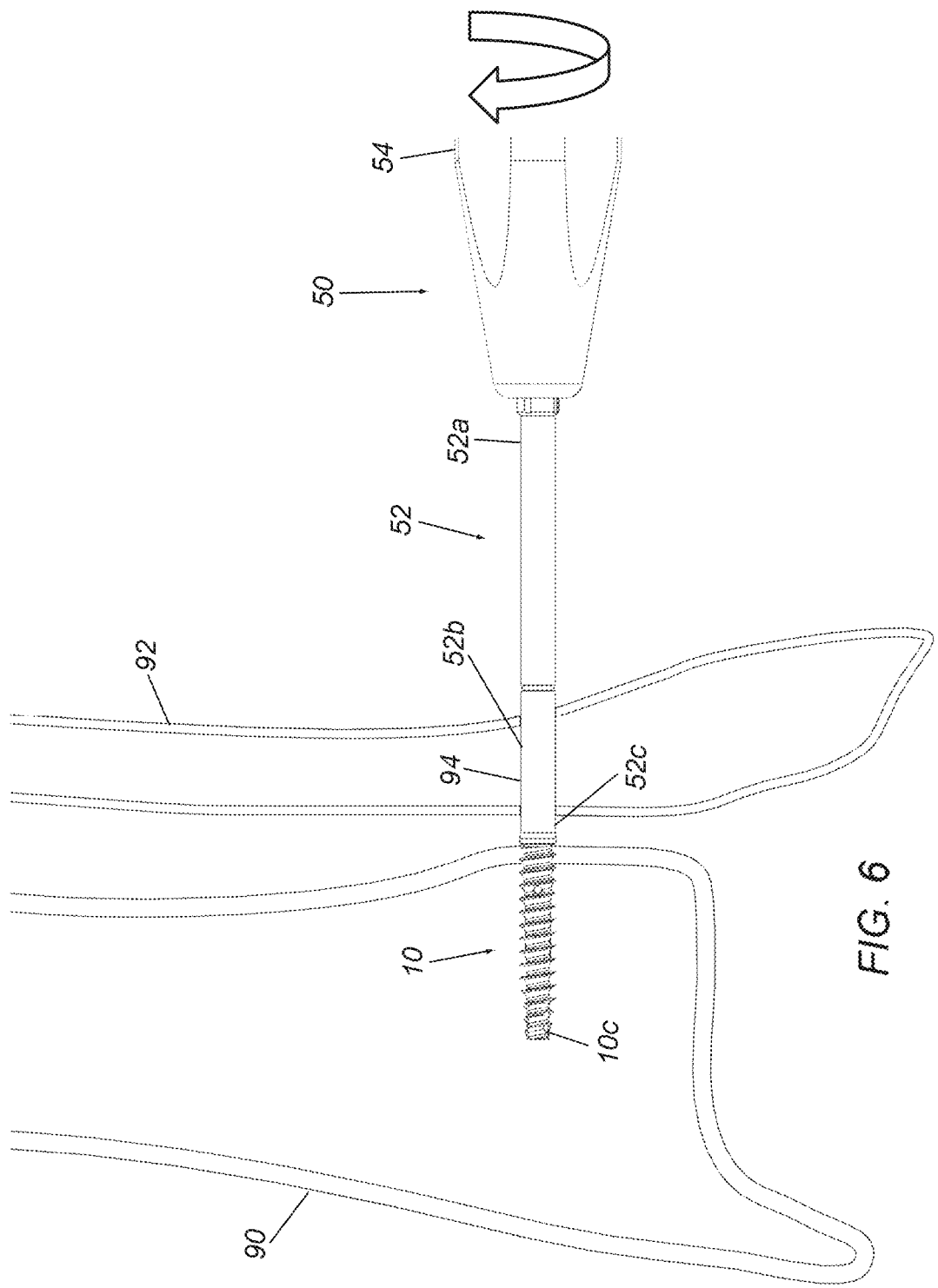
Figure 9:
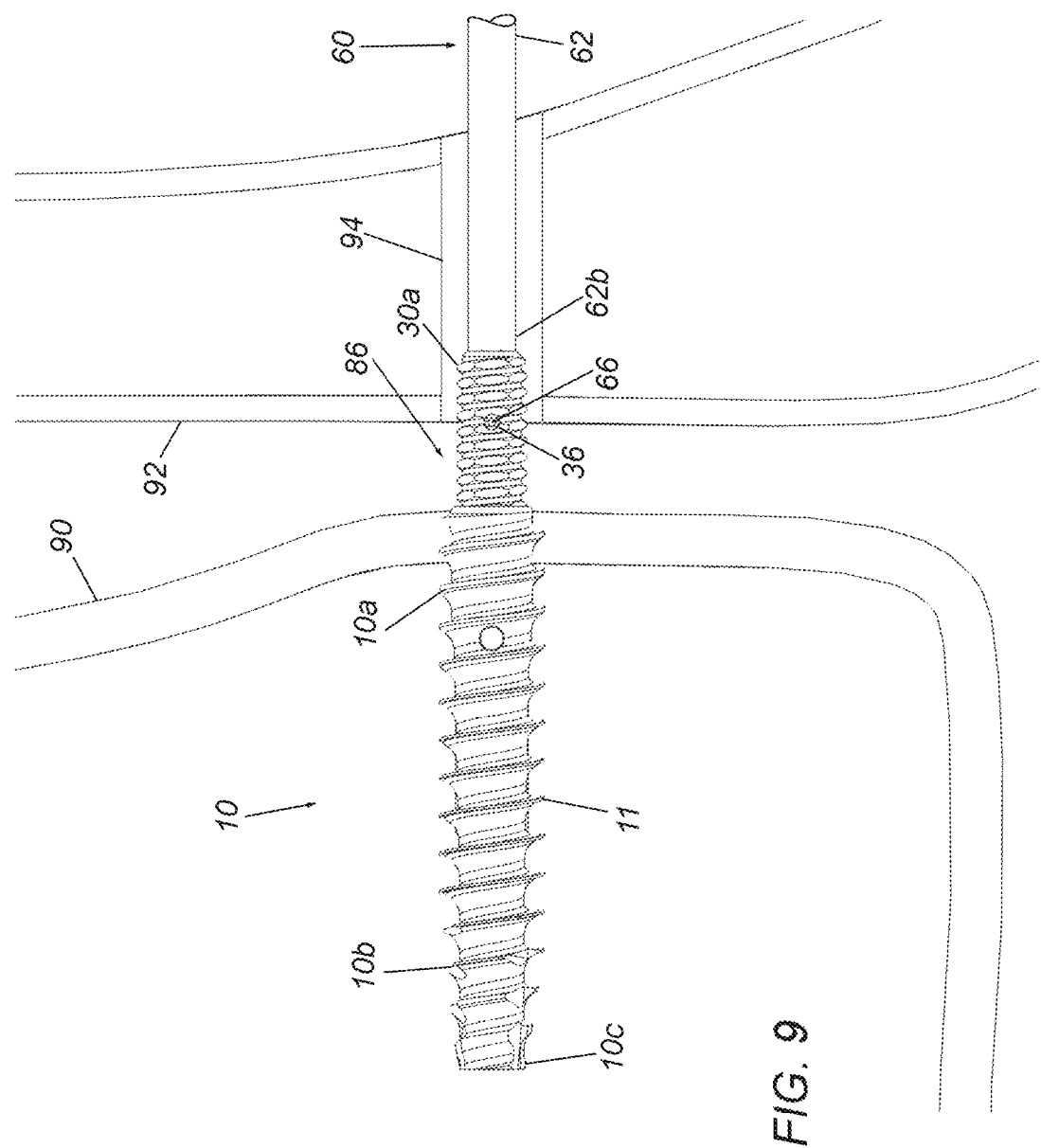
Figure 10:
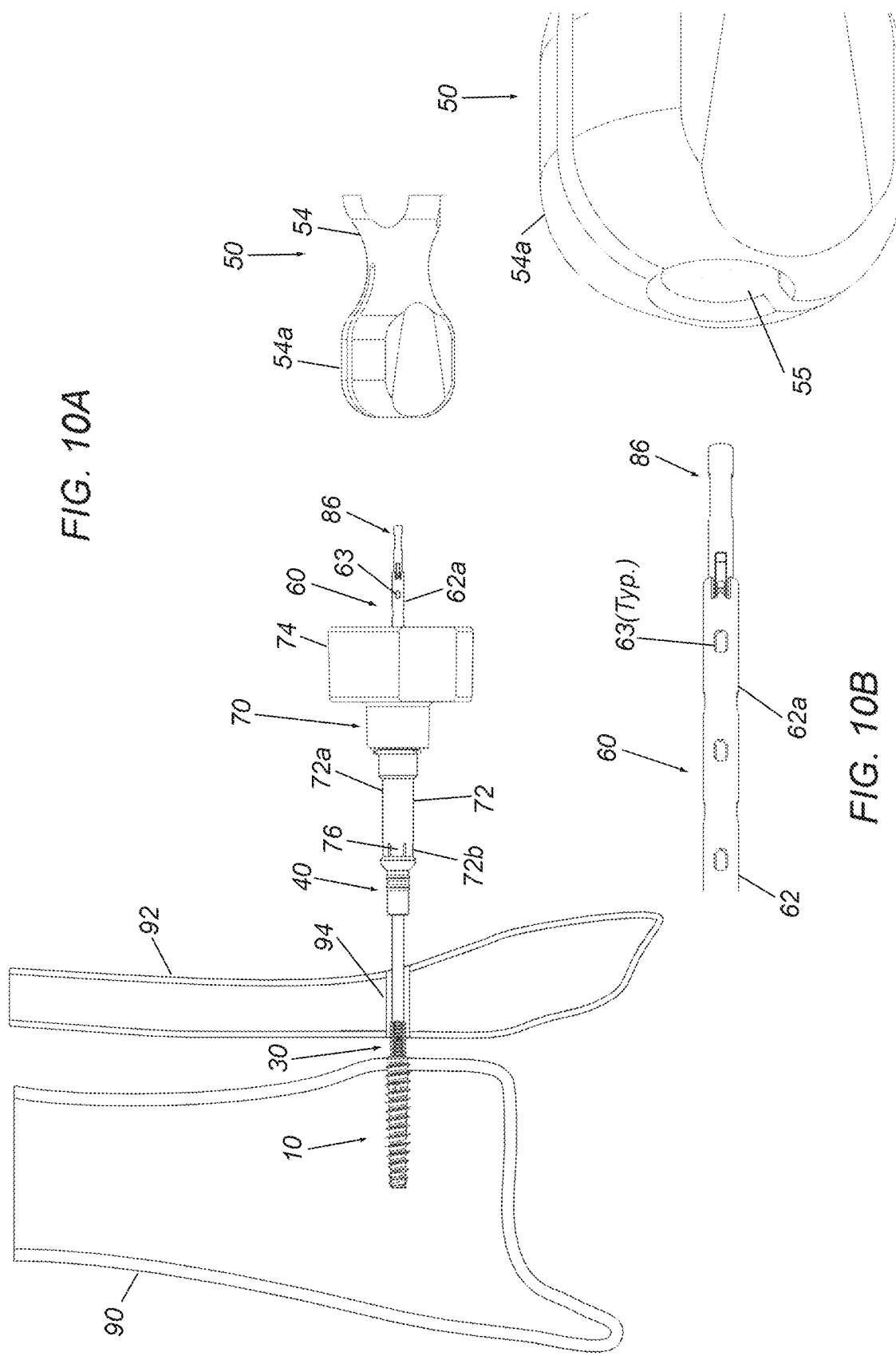

Turning to FIG. 6, the first anchor 10 may then be introduced through the clearance hole 94 and threaded into the tibia 90 via the pilot hole 96 to a desired depth. For example, as described elsewhere herein, the first anchor 10 may be secured to the distal end 52b of the outer shaft 52 of the first driver tool 50 with the first component 30 (not shown) inserted into the first anchor 10 and outer shaft 52. Once the distal tip 10c of the first anchor 10 engages the tibia 90, the first driver tool 50 may be rotated and advanced to thread the first anchor 10 into the tibia 90 to a desired depth, e.g., such that the proximal end 10a of the first anchor 10 is substantially flush with the outer surface of the tibia 90 (e.g., as best seen in FIG. 9). As can be seen, the clearance hole 94 drilled through the fibula 92 has sufficient size to accommodate the outer shaft 52 of the first anchor driver tool 50 passing therethrough to thread the first anchor 10 into the tibia 90.

Figure 7:
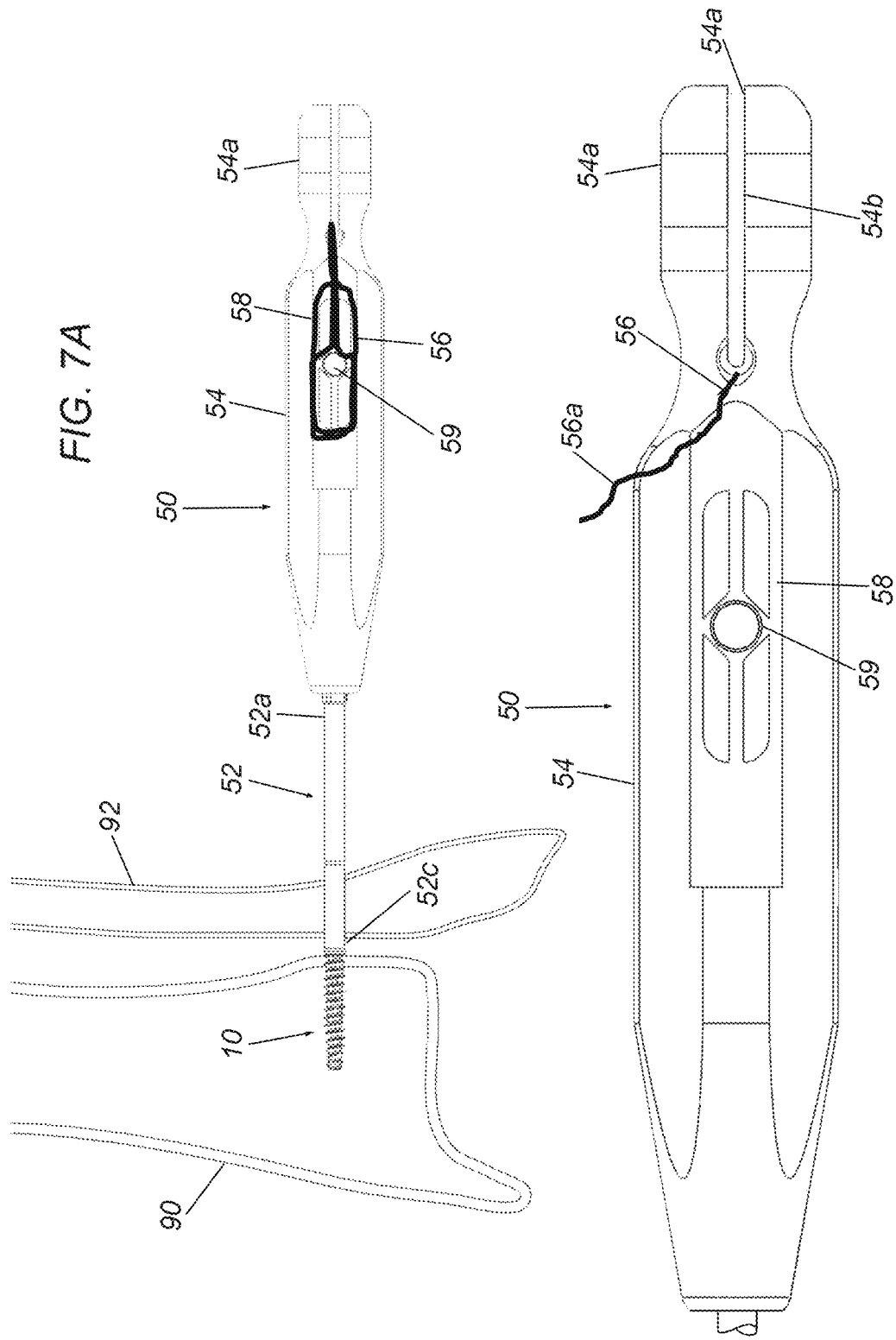

Turning to FIGS. 7A and 7B, once the first anchor 10 is threaded into the tibia 90 to the desired depth, the first driver tool 50 may be removed. Since the first anchor 10 is secured to the outer shaft 52, the user first releases the first anchor 4 from the first driver tool 50, e.g., by releasing the suture 56 from the cleat 58, and then the first driver tool 50 may be withdrawn, as shown in FIG. 7. As the first driver tool 50 is withdrawn, the free end 56a of the suture 56 may retreat into the handle 54 and outer shaft 52 until the suture 56 is disengaged from the flexible link 20 (or other structure around which the suture 56 is looped).

Figure 8:
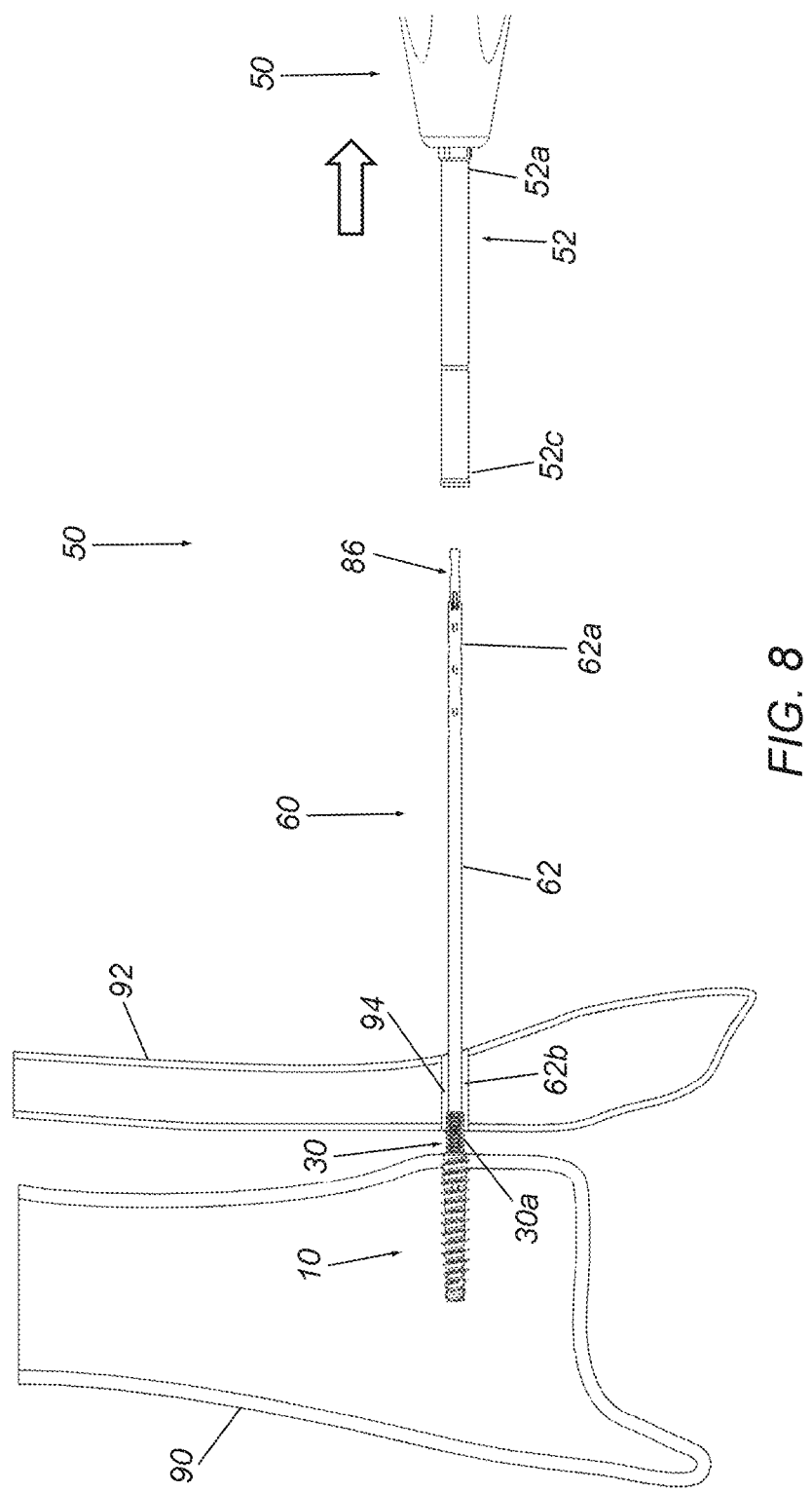

As can be seen in FIG. 8, as the first anchor driver tool 15 is being withdrawn from its first anchor 10, the proximal end 30a of the first component and the guide tube 60 are exposed.

FIG. 9 shows an exemplary embodiment of the interface between the first anchor 10, the first component 30 of the second anchor 18, and the guide tube 60. In this close-up view, it can be seen that the first component 30 of the second anchor 18 has an external profile capable of receiving driving torque from the first anchor driver tool 50 and then transmitting that torque to an internal feature of the same profile in the proximal region of the first anchor 4. This close-up view also shows the inter-locking connectors 36, 66 used to attach the guide tube 60 to the first component 30 of the second anchor 18 until released by the user.

Turning to FIGS. 10A and 10B, the second component 40 of the second anchor 18 may be advanced over the guide tube 60 and into the hole 94 in the fibula 92, using the second installation driver tool 70. As described elsewhere herein, the second component 40 may be secured to the distal end 72b of the shaft 72 using one or more detents or other connectors 76. To control rotational and other motion of the guide tube 60, the back side 54a of the handle 54 of the first anchor driver tool 50 may include a receptacle of grippy material 55 that may be slid over the proximal end 62a of the guide tube 60. In addition, the guide tube 60 may have features 63 designed to enhance gripping the guide tube 60 within the receptacle 55. Alternatively, another tool, e.g. a set of pliers, a clamp, or other tool (not shown) may be used to hold the proximal end 62a of the guide tube 60.

Figure 11:
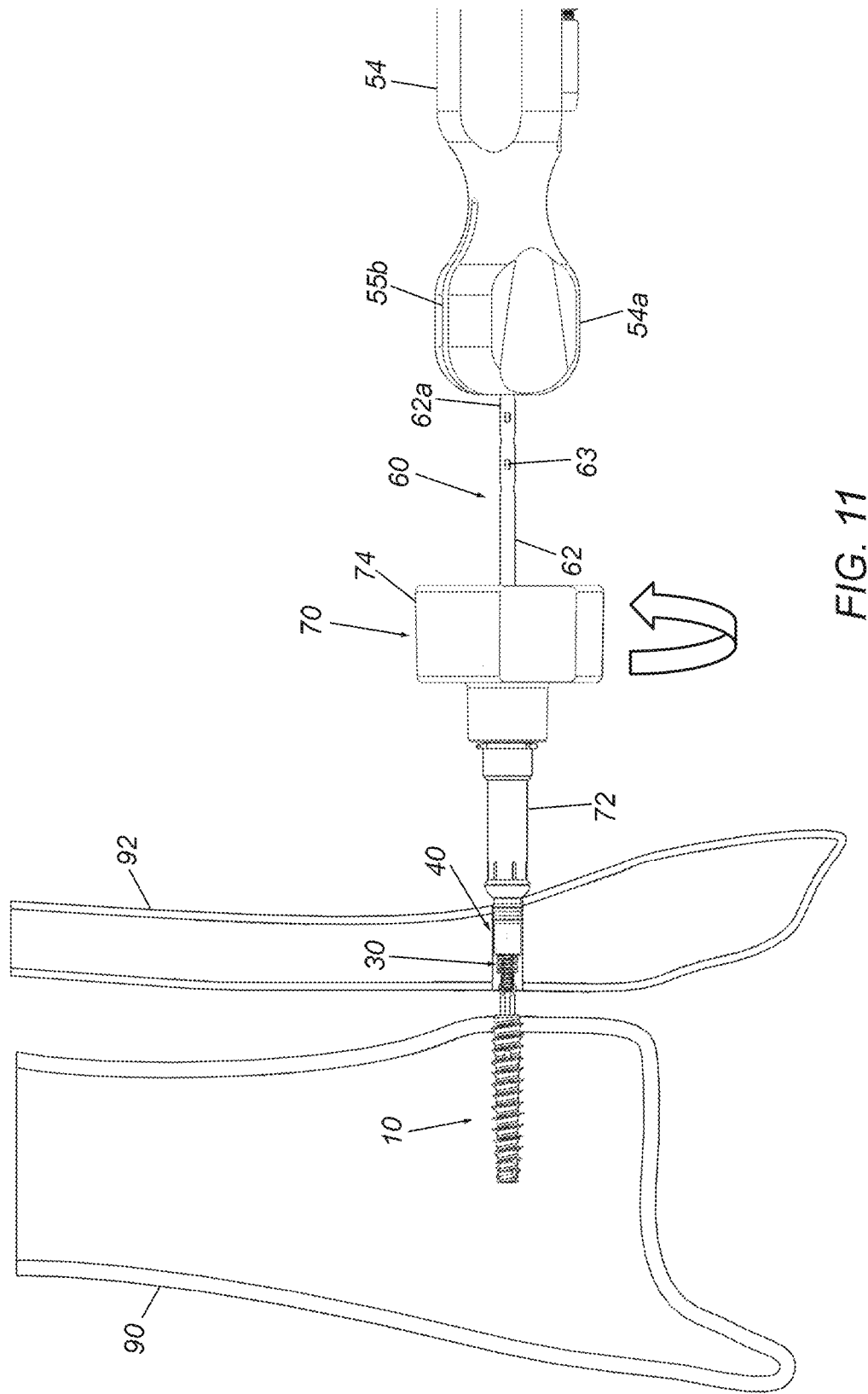

Turning to FIG. 11, with the guide tube 60 secured using the back end 54a of the handle 54, the first component 30 of the second anchor 18 may remain substantially stationary as the second component 40 of the second anchor 18 is tightened down using the second installation tool 70. Initially, the second component 40 and second installation tool 70 may be advanced axially over the guide tube 60 without rotation until the second component 40 reaches the proximal end 30a of the first component 30. At this point, the second installation tool 70 may be rotated to thread the second component 40 over the first component 30 of the second anchor 18, thereby slidably engaging the threads 32, 46 (e.g., best seen in FIG. 3). Note that, as the second component 40 of the second anchor 18 is tightened down, the head 48 may contact the outer surface of the fibula 92 limiting further advancement of the second component 40. Further rotation causes first component 30 to move proximally, i.e., disengaging the distal end 30b of the first component 30 from the first anchor 10 and retracting it until the flexible link 20 is exposed and reaches its design length, at which point, further tightening of the second component 40 of the second anchor 18 reduces the gap between the two bones 90, 92. It will be appreciated that the axial location of the second anchor 18 may be adjusted as desired to provide a desired gap between the bones 90, 92 with rotation of the second component 40 causing the first component 30 to move axially within the hole 94 in the fibula and move the fibula 94 closer or further away from the tibia 90.

Figure 12:
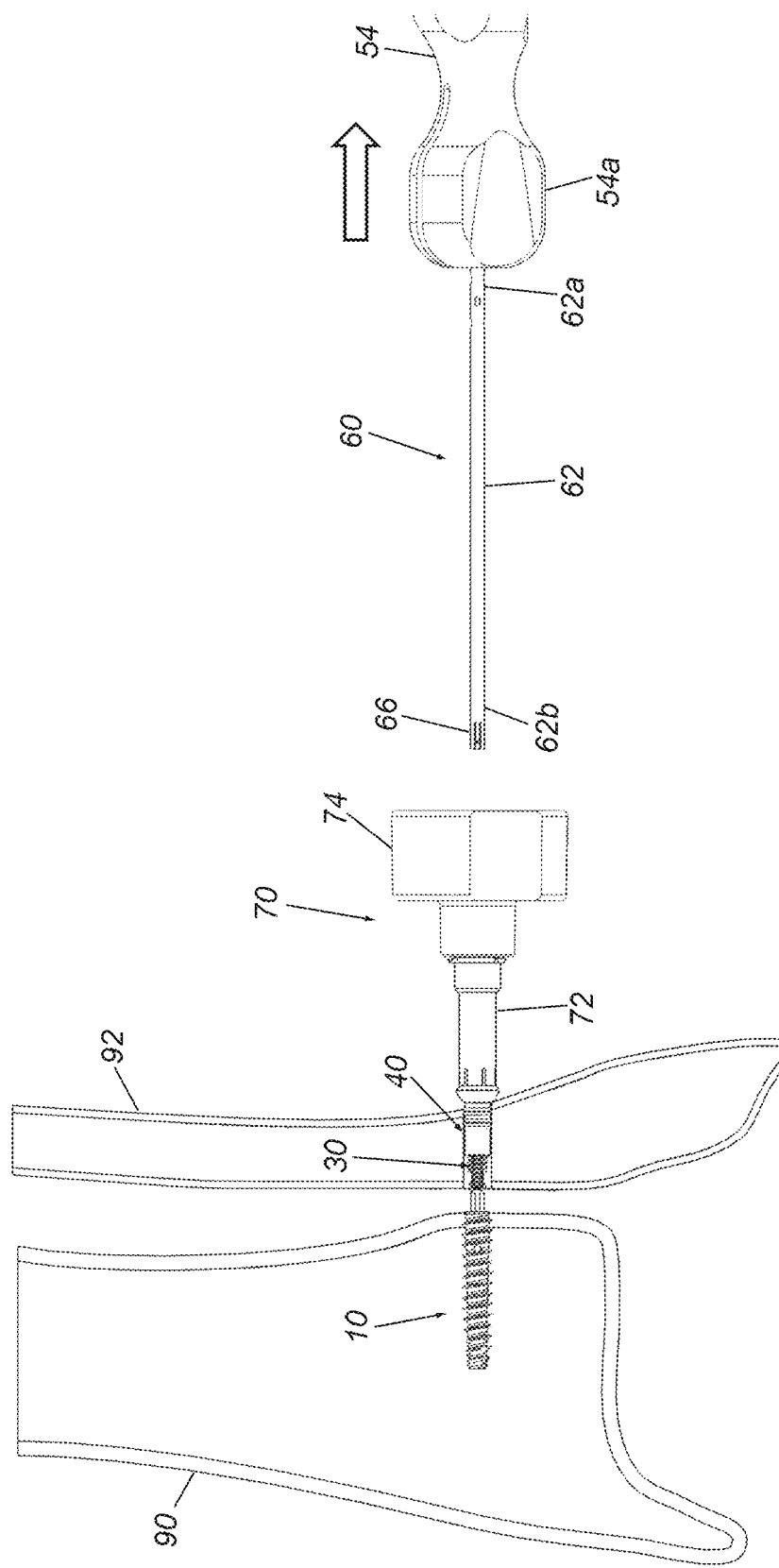

Turning to FIG. 12, once the implant 10 and bones 90, 92 are positioned as desired, the tools may be removed. For example, the guide tube 60 may be retracted using the first driver tool 50 after the second component 40 of the second anchor 18 has reached its fully-installed state. To accomplish this, the user first removes the lock member 86 (not shown, see, e.g., FIGS. 10A and 10B), whereupon the connectors 66 are disengaged from the pockets 36 in the first component 30 (e.g., as shown in FIGS. 17C-17E), e.g., due to the bias of the connectors 66 to the inward orientation. The guide tube 60 may then be freely withdrawn through the shaft 72 of the second installation tool 70, as shown in FIG. 12.

Turning to FIG. 13, the second installation tool 70 may then be disengaged from the second component 40 and removed. As described elsewhere herein, the shaft 72 of the second installation tool 70 may include retention features or other connectors 66 on the distal end 72b that retain the second component 40 of the second anchor 18 on the second installation tool 70 until sufficient force is applied to un-snap it.

Figure 14:
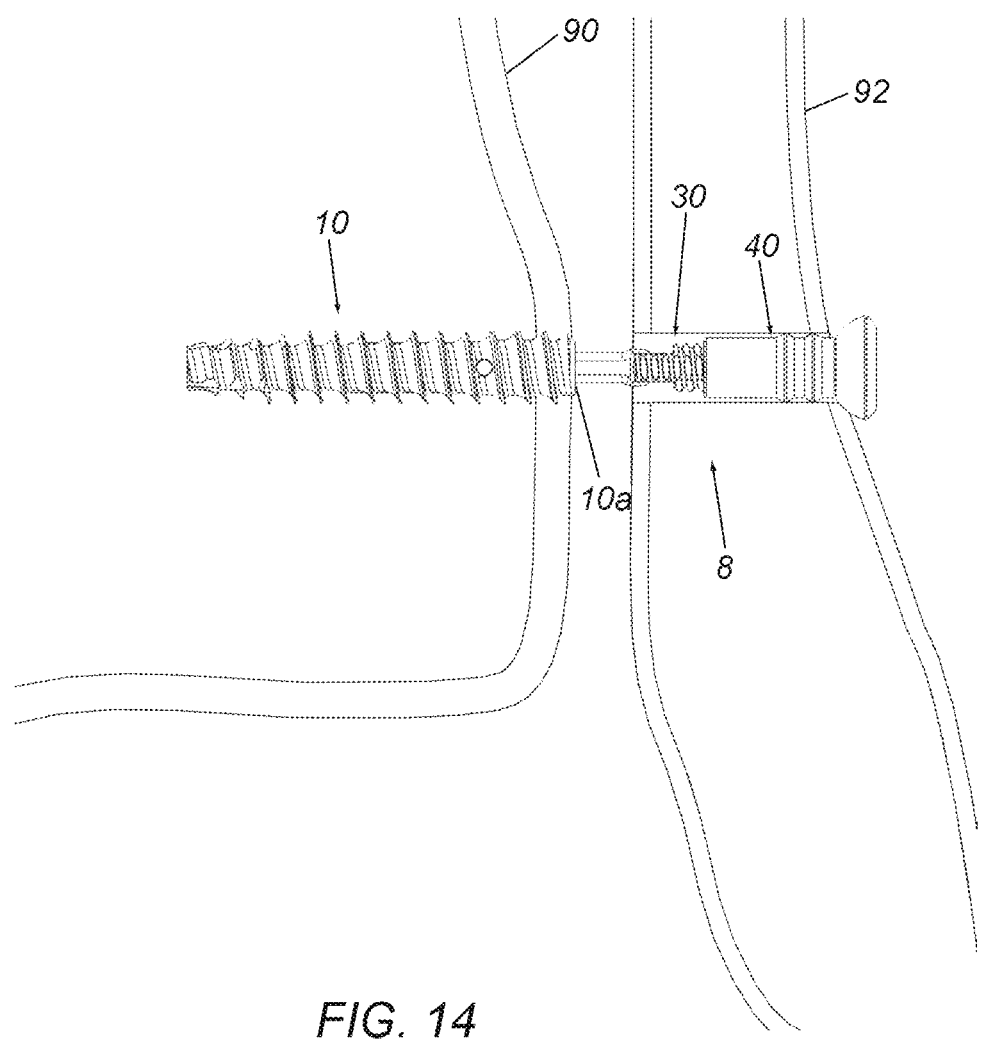

FIG. 14 shows the exemplary embodiment of the implant assembly 8 in its fully-installed state. As shown, in a desired installation, the proximal end 10a of the first anchor 4 may be substantially flush with the surface of the cortex of the tibia 90.

Figure 15:
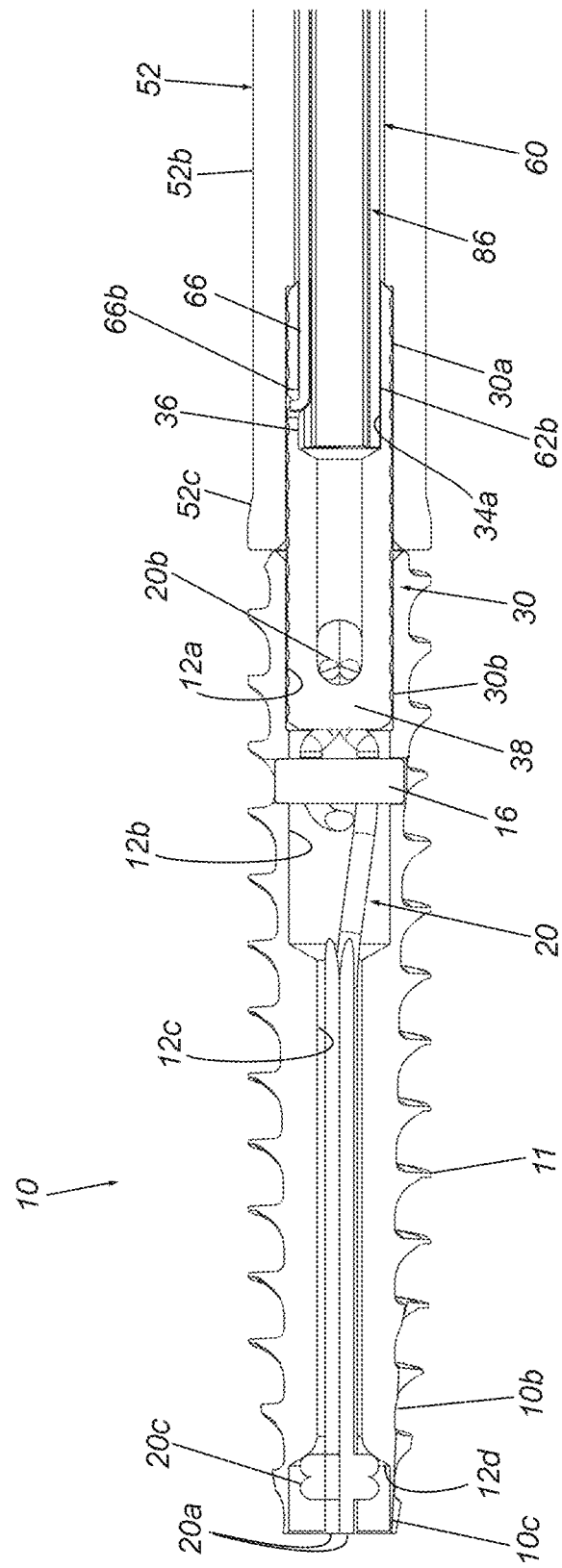
FIG. 15 is a cross-sectional view of the first anchor, distal component of the second anchor, flexible link, and the guide tube as they are housed in the first anchor driver tool.

FIG. 15 shows an exemplary embodiment of the first driver tool 50 and the components housed inside it during early installation (e.g., during the steps shown in FIGS. 6, 7A, and 7B) in cross-section view. Note the interaction between the first anchor 10, the first component 30 of the second anchor 18, and the first driver tool 50—the external hex of the first component 30 of the second anchor 18 spans the internal hex features in the proximal region 12a of the bore 12 within the first anchor 10 and the socket within the distal end 52b of the first driver tool 50. This allows torque applied to the first driver tool 50 by the surgeon to be transmitted to the first component 30 of the second anchor 18. The first component 30 of the second anchor 18 then applies torque to the first anchor 10 to drive it into the first bone (not shown). This cross-sectional view also shows the placement of the guide tube 60 and lock member 86 within the first driver tool 50 during early installation.

Figure 16:
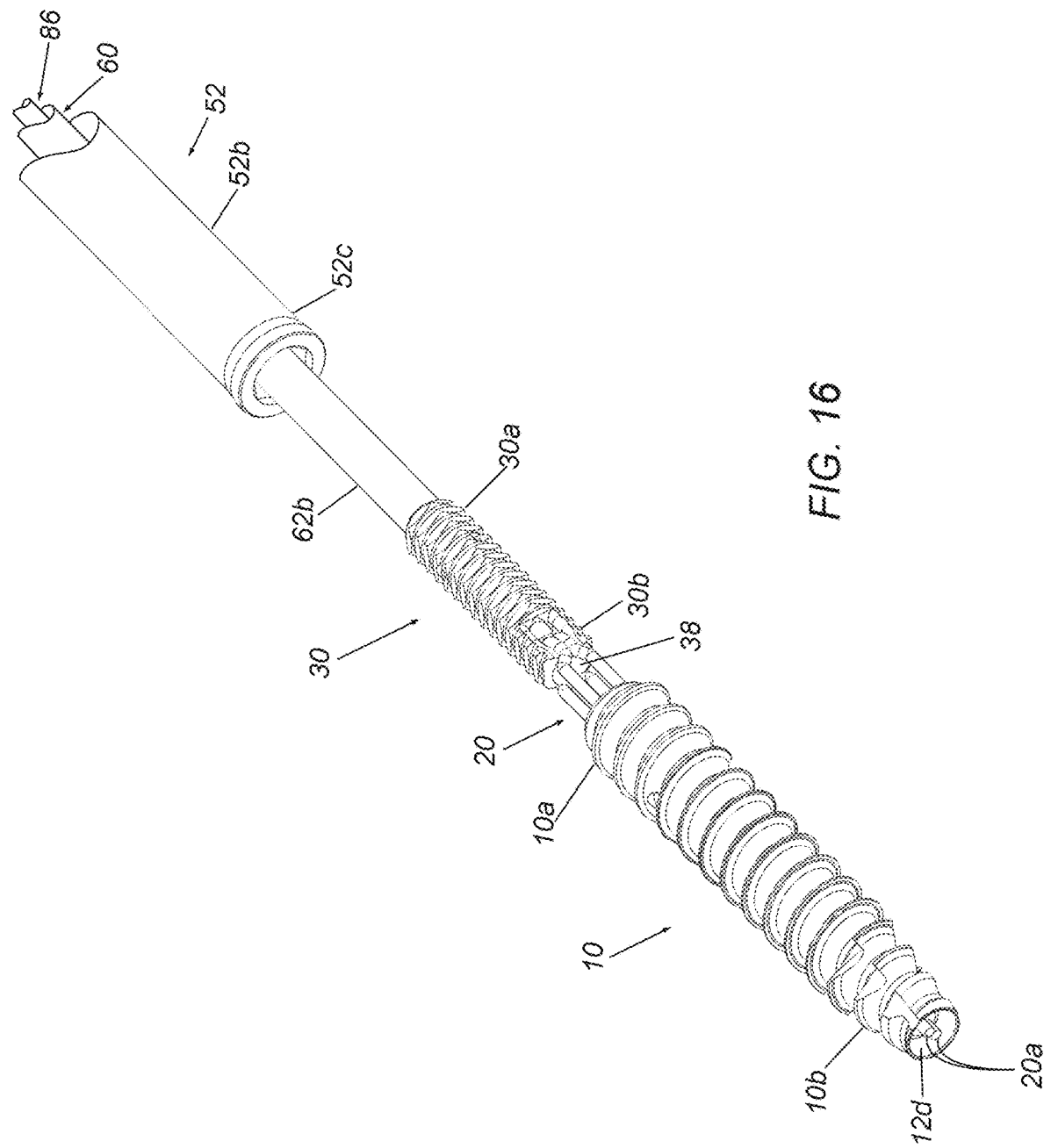
FIG. 16 is a detail of the drive interface with which the first anchor driver tool imparts torque to the distal piece of the second anchor, which in turn imparts torque to the first anchor.

FIG. 16 shows an exemplary embodiment of the first anchor 10, first driver tool 50, flexible link 20, first component 30 of the second anchor 18, and guide tube 60. This view makes the external hex of the first component 30 of the second anchor 18 visible, as well as the corresponding internal hex feature in the distal tip 52c of the first driver tool 50.

While the invention is susceptible to various modifications, and alternative forms, specific examples thereof have been shown in the drawings and are herein described in detail. It should be understood that the invention is not to be limited to the particular forms or methods disclosed, but to the contrary, the invention is to cover all modifications, equivalents and alternatives falling within the scope of the appended claims.

We claim:

1. A method for approximating first and second bones relative to one another, comprising:
    advancing a first anchor having a first component into a first bone by applying a force to a driver tool coupled to a first component of a second anchor;
    disengaging the first component of the second anchor from the first anchor to expose a flexible link extending between the first anchor and the first component of the second anchor;
    withdrawing the second anchor until the flexible link connecting the first anchor to the second anchor reaches its designed predetermined length, thereby positioning the second anchor in a second bone;
    affixing a second component of the second anchor to the first component of the second anchor such that a head of the second component engages the second bone or a bone support on the second bone; and
    adjusting a location of the second component along the first component to adjust the approximation between the first and second bones.

2. The method of claim 1, wherein the first and second bones being approximated are a tibia and a fibula following an injury of the ankle syndesmosis.

3. The method of claim 1, wherein the first component comprises a distal end received in a first socket in the first anchor to couple the first component to the socket.

4. The method of claim 3, wherein the first component comprises a proximal end received in a second socket in a distal end of the driver tool to couple the first component to the driver tool.

5. The method of claim 1, wherein disengaging the first component of the second anchor from the first anchor comprises:
    disengaging a securing feature between the driver tool and the first anchor; and
    withdrawing the driver tool while the first component of the second anchor remains within the second bone.

6. The method of claim 5, wherein a guide member extends proximally from the first component within the driver tool and wherein the guide member is exposed when the driver tool is withdrawn.

7. The method of claim 6, wherein affixing a second component of the second anchor to the first component comprises:
    directing the second component over the guide member until the second component engages one or more features on the first component; and
    advancing the second component over the first component using the one or more features.

8. The method of claim 7, wherein the one or more features comprise external threads on the first component, wherein the second component comprises internal threads, and wherein advancing the second component over the first component comprises threading the second component over the first component.

9. The method of claim 7, wherein the second component is carried on a distal end of an installation tool and wherein the installation tool is directed over the guide member to direct the second component over the guide member.

10. The method of claim 9, further comprising disengaging the installation tool from the second component after adjusting the location of the second component along the first component.

11. The method of claim 6, wherein a distal end of the guide member is coupled to the first component, the method further comprising:
    disengaging the guide member from the first component after adjusting the location of the second component along the first component; and
    removing the guide member.

12. The method of claim 11, wherein the guide member distal end is coupled to the first component by a plurality of detents on the guide member distal end received in respective pockets in the first component, and wherein disengaging the guide member comprises removing a lock member from the guide member whereupon the detents automatically disengage from the respective pockets to allow the guide member to be removed.

13. A method for approximating first and second bones relative to one another, comprising:
    providing a driver tool including a shaft having a distal end, a first anchor, a first component of a second anchor including a distal end received in a first socket of the first anchor, and a proximal end received in a second socket in the driver tool shaft distal end, and a guide member coupled to the first component proximal end and extending proximally through the driver tool shaft, the first anchor and first component secured relative to the driver tool shaft distal end;

advancing the first anchor towards a first bone through a hole in a second bone adjacent the first bone;

applying torque to the driver tool to direct the first anchor into the first bone, the torque transferred from the driver tool shaft to the first anchor via the first component of the second anchor;

releasing the first anchor and first component from the driver tool shaft distal end;

withdrawing the driver tool, thereby exposing the guide member;

directing a second component of the second anchor over the guide member to the first component;

advancing the second component of the second anchor over the first component, thereby causing the first component distal end to withdraw from the first socket and expose a flexible link extending between the first anchor and the first component of the second anchor;

advancing the second component further, thereby extending the flexible link to a predetermined length and positioning the second anchor in the hole in the second bone;

engaging a head of the second component with the second bone or a bone support on the second bone; and adjusting a location of the second component along the first component to adjust the approximation between the first and second bones.

14. The method of claim 13, wherein the first and second bones being approximated are a tibia and a fibula following an injury of the ankle syndesmosis.

15. The method of claim 13, further comprising:

disengaging the guide member from the first component after adjusting the location of the second component along the first component; and removing the guide member.

16. The method of claim 13, wherein the guide member distal end is coupled to the first component by a plurality of detents on the guide member distal end received in respective pockets in the first component, and wherein disengaging the guide member comprises removing a lock member from the guide member whereupon the detents automatically disengage from the respective pockets to allow the guide member to be removed.

17. The method of claim 13, wherein the second component is carried on a distal end of an installation tool and wherein the installation tool is directed over the guide member to direct the second component over the guide member.

18. The method of claim 17, further comprising disengaging the installation tool from the second component after adjusting the location of the second component along the first component.

* * * * *